United States Patent [19]

Baserga et al.

[11] Patent Number: 5,714,170
[45] Date of Patent: Feb. 3, 1998

[54] METHOD OF INDUCING RESISTANCE TO TUMOR GROWTH

[75] Inventors: Renato Baserga, Ardmore; David Abraham, Wynnewood; Mariana Resnicoff, Philadelphia, all of Pa.

[73] Assignee: Thomas Jefferson University, Philadelphia, Pa.

[21] Appl. No.: 340,732

[22] Filed: Nov. 16, 1994

[51] Int. Cl.$^6$ ............................................. A61K 35/12
[52] U.S. Cl. ..................... 424/573; 424/572; 424/422; 424/423; 424/424; 424/425; 424/93.2; 424/93.21; 604/890.1; 435/91.1; 435/285.1; 536/23.1
[58] Field of Search ........................... 435/285.1, 91.1; 536/23.1; 514/44; 424/93.2, 93.21, 573, 422, 423, 424, 425, 572; 604/890.1

[56] References Cited

U.S. PATENT DOCUMENTS

| | | | |
|---|---|---|---|
| 5,077,059 | 12/1991 | Mishima et al. | 424/573 |
| 5,262,308 | 11/1993 | Baserga | 435/69.1 |
| 5,272,082 | 12/1993 | Santoli et al. | 435/240.2 |

FOREIGN PATENT DOCUMENTS

91/17253  11/1991  WIPO.

OTHER PUBLICATIONS

Becker et al. 1992, EMBO J. 8(12): 3685–3691.
Brown, D. 1995, "Gene Therapy 'Oversold' By Researchers, Journalists" in: *The Washington Post*, 8 Dec. 1995, pp. 1 and A22.
Kolata, G., 1995, "In the rush toward gene therapy, some see a high risk of failure", in: *The New York Times*, 25 Jul. 1995, p. C3.
Marshall, E., 1995, Science 269: 1050–1055.
Miller et al. 1994, Parasitology Today, 10(3): 92–97.
Wu–Pong, S. 1994, Pharmaceutical Technology, Oct. 1994, pp. 102, 104, 106, 108, 110–112, and 114.
Tseng et al. 1994, Cancer Gene Therapy, 1(1): 65–71.
Conley, F. K. 1974, J. Neurosurg. 41: 332–338.
Ray et al. Ca$^{2+}$ antagonists inhibit DNA fragmentation and toxic cell death induced by acetaminophen *The FASEB Journal* 1993 7:453–463.
Sell et al., Simian virus 40 large tumor antigen is unable to transform mouse embryonic fibroblasts lacking type 1 insulin–like growth factor receptor *Proc. Natl. Acad. Sci. USA* 1993, 90:11217–11221.
Sell et al., Effect of a Null Mutationof the Insulin–Like Growth Factor I Receptor Gene on Growth and Transformation of Mouse Embryo Fibroblasts *Mol. Cell. Biol.* 1994, 14:3604–3612.
Valentinis et al., The role of the insulin–like growth factor I receptor in the transformation by simian virus 40 T antigen *Oncogene* 1994, 9:825–831.
Coppola et al., A Functional InsulinOLike Growth Factor I Receptor is Required for the Mitogenic and Transforming Activities of the Epidermal Growth Factor Receptor *Mol. Cell. Biol.* 1994, 14:4588–4594.

Resnicoff et al., Rat Glioblastoma Cells Expressing an Antisense RNA to the Insulin–like Growth Factor–1 (IGF–1) Receptor are Nontumorigenic and Induce Regression o Wild–Type Tumors *Cancer Res.* 1994, 54:2218–2222.
Resnicoff, M., et al., Growth Inhibition of Human Melanoma Cells in Nude Mice by Antisense Strategies to the Type 1 Insulin–like Growth Factor Receptor *Cancer Res.* 1994, 54:4848–4850.
Harrington et al., c–Myc–induced apoptosis in fibroblasts is inhibited by specific cytokines *EMBO J.* 1994, 13:3286–3295.
Goldring and Goldring, Cytokines and Cell Growth Control *Crit. Rev. Eukaryot. Gene Expr.* 1991, 1:301–326.
Baserga and Rubin, Cell Cycle and Growth Control *Crit. Rev. Eukaryot. Gene Expr.* 1993, 3:47–61.
Pietrzkowski et al., Constitutive Expression of Insulin–like Growth Factor 1 and Insulin–like Growth Factor 1 Receptro Abrogates All Requirements for Exogenous Growth Factors *Cell Growth & Diff* 1992, 3:199–205.
Pietrzkowski et al., Roles of Insulinlike Growth Factor 1 (IGF–1) and the IGF–1 Receptor in Epidermal Growth Factor–Stimulated Growth of 3T3 Cells *Mol. Cell. Biol.* 1992, 12:3883–3889.
Buttyan, R., et al., Induction of the TRPM–2 Gene in Cells Undergoing Programmed Death *Mol Cell Biol* 1989, 9:3473–3481.
Kaufmann, S.H., Induction of Endonucleolytic DNA Cleavage in Human Acute Myelogenous Leukemia Cells by Etoposide, Camptothecin, and Other Cytotoxic Anticancer Drugs: A Cautionary Note *Cancer Res* 1989, 49:5870–5878.
Barry, M.A., et al., Activiation of Programmed Cell Death by Cisplatin, Other Anticancer Drugs, Toxins and Byperthermia *Biochem Pharmacol*, 1990, 40:2353–2362.
Bursch, W., et al., Determination of the length of the histological states of apoptosis in normal liver and in altered hepatic foci of rats *Carcinogenesis* 1990, 11:847–853.
Lange et al., IL–4–and IL–5–Dependent Protective Immunity to Onchocerca Volvulus infective Larvae in BALB/ cBYJ mice *J. Immunol.* 1994, 153:205–211.
Lanza et al., Xenogeneic Humoral Responses to Islets Transplated in Biohybrid Diffusion Chambers *Transplantation*, 1994, 57:1371–1375.
Trojan et al., Treatment and Prevention of Rat Glioblastoma by Immunogenic C6 Cells Expressing Antisense Insulin–Like Growth Factor I RNA *Science* 1993, 259:94–97.
Martin et al., Development of a in Vitro Assay for the Survival of Cells Suspended from BA1112 Rat Sarcomas *Eur. J. Cancer Clin. Oncol.* 1983, 19:791–797.
Preston et al Regulation of Apoptosis by Low Serum in Cells of Different Stages of Neoplastic Progression *Cancer Res.* 1994 54:4214–4223.

*Primary Examiner*—Christopher S. F. Low
*Attorney, Agent, or Firm*—Woodcock Washburn Kurtz Mackiewicz & Norris LLP

[57] ABSTRACT

A method of inducing resistance to tumor growth comprising placing tumor cells in culture supplemented with an agent in a diffusion chamber thereby producing a cell-containing chamber, inserting the chamber into a mammal for a therapeutically effective time, thereby inducing resistance to tumor growth.

7 Claims, 10 Drawing Sheets

Diffusion Chamber

```
        190                        200
CysGlnLysMetCysProSerThrCysGlyLysArgAlaCysThrGluAsnAsnGluCysCysHisProGluCys
TGCCAGAAAATGTGCCCAAGCACGTGTGGGAAGCGGGCCTGCACCGAGAACAATGAGTGCTGCCACCCGAGTGC  750
                220                        230
LeuGlySerCysSerAlaProAspThrAlaCysValAlaAlaCysArgHisTyrTyrTyrAlaGlyValCys
CTGGGCAGCTGCAGCGCGGCCTGACAACGCACGGCCTGTGTAGCTGCCGCCACTACTACTATGCCGGTGTCTGT

ValProAlaCysProProAsnThrTyrArgPheGluGlyTrpArgCysValAspArgAspPheCysAlaAsnIle
GTGCCTGCCTGCCCGCCCAACACCTACAGGTTTGAGGGCTGGCGCTGTGTGGACCGTGACTTCTGCGCCAACATC  900
          260                         270                        280
LeuSerAlaSerSerAspGlyGluPheValIleHisAspGlyGluCysMetGlnGluCysProSerGly
CTCAGCGCCTCCAGCGACGGCGAGTTCGTGATCCACGATGGAGAGTGCATGCAGGAGTGCCCCTCGGGC
                290                       300
PheIleArgAsnGlySerGlnSerMetTyrCysIleProCysGluGlyProCysProLysValCysGluGlu
TTCATCCGCAACGGCAGCCAGAGCATGTACTGCATCCCCTGTGAAGGTCCTTGCCCGAAGGTCTGTGAGGAAGAA  1050
                          320                       330
LysLysThrIleAspSerValThrSerAlaGlnMetLeuGlnGlyCysThrIlePheLysGlyAsnLeu
AAGAAAACAATTGATTCTGTTACTTCTGCTCAGATGCTCCAAGGATGCACCATCTTCAAGGCAATTTG
            340                        350
LeuIleAsnIleArgArgGlyAsnAsnIleAlaSerGluLeuLysValSerPheLeuLysAsnLeuArgGluIleLeuThr
CTCATTAACATCCGACGGGGGAATAACATTGCTTCAGAGCTGAAAGTTTCATTCCTAAAAAACCTTCGCGAGATTCTGACG  1200
         360                        370                           380
GlyTyrValLysIleArgHisSerHisAlaLeuValSerPheLeuLysSerPheLeuValSerArgGluLeuLeuGly
GGCTACGTGAAGATCCGGCATTCTCATGCCTTGGTCTCCTTTCTTAAAAGCTTCCTCGTCTCATCCTAGGA
          390                         400
GluGluLeuGluGlyAsnTyrSerPheTyrValLeuAspAsnGlnAsnLeuGlnLeuTrpAspAsp
GAGGAGCTAGAAGGGAATTACTCCTTCTACGTCCTCGACAACCAGAACTTGCAGCAACTGTGGGAC  1350
```

FIG. 4B

```
      410                    420                    430
HisArgAsnLeuThrIleLysAlaGlyMetTyrPheAlaPheAsnProLysLeuCysValSerGluIleTyr
CACCGCAACCTGACCATCAAGGCAGGGAAAATGTACTTTGCTTTCAATCCCAAATTATGTGTTTCCGAAATTTAC 1500
      440                    450
ArgMetGluValThrGlyThrLysGlyArgGlnSerLysGlyAspIleAsnThrThrArgAsnGlyGluArg
CGCATGGAGGTAACGGGCACGAAGGGCCGCCAAAGCAAAGGGGACATAAACACCACAGGAACAACGGGGGAGAGA 460                    470                    480
AlaSerCysGluSerAspValLeuHisPheThrSerThrThrThrSerLysAsnArgIleIleIleThrTrpHis
GCCTCCTGTGAAAGTGACGTCCTGCATTTCACCTCCACCACCACGTCGAAGAATCGCATCATCATAACCTGGCAC 1650
      490                    500
ArgTyrArgProProAspTyrArgAspLeuIleSerPheThrValTyrTyrLysGluAlaProPheLysAsnVal
CGGTACCGGCCCCCTGACTACAGGGATCTTATCAGCTTTACCGTTTACTACAAGGAAGCACCCTTTAAGAATGTC 510                    520                    530
ThrGluTyrAspGlyGlnAlaCysGlySerAsnSerTrpAsnMetValAspValAlaValThrTyrValLysAsnLys
ACAGAGTATGATGGGCAGGCATGCGGCTCCAACAGCTGGAACATGGTGGACGTGGCCGTTACGTACGTTAAGAACAAG 540                    550
AspValProGlyIleLeuLeuHisGlyLeuLeuLysProTrpThrGlnTyrAlaValTyrValLysAlaValThr
GACGTGCCAGGCATCCTACTACATGGGCTGCTGAAGCCCTGGACTCAGTACGCCGTTTACGTCAAGGCTGTGACC 1800
      560                    570                    580
LeuThrMetValGluAsnAspHisIleArgGlyAlaAlaLysSerGluIleLeuValTyrIleArgThrAsnAlaSerVal
CTCACCATGGTGGAGAACGACCATATCCGTGGGGCCAAGAGTGAGATCTTGTACATTCGCACCAATGCTTCAGTT 590                    600
ProSerIleProLeuAspValLeuSerAlaSerSerGlnLeuIleValTrpAsnProSer
CCTTCCATTCCTCTTGGACGTTCTTTCAGCATGAACTCCTCTTCCCAGTTAATCGTGAAGTGGAACCCCTCT 1950
      610                    620                    630
LeuProAsnGlyAsnLeuSerTyrTyrIleValArgGlnProGlnAspGlyTyrLeuTyrArgHis
CTGCCCAACGGCAACCTGAGTTACTACATTGTGCGGCAGCCTCAGGACGGCTACCTTTACCGGCAC
```

FIG. 4C

```
                    640                                                650
AsnTyrSerLysAspLysIleProIleArgLysTyrAlaAspGlyThrIleAspIleGluValThrGlu
AATTACTGCTCCAAAGAGACAAAATCCCCATCAGGAAGTATGCCGACGGCACCATTGAGGAGGTCACAGAG    2100

660                                          670                    680
AsnProLysThrGluValProLysThrCysGlyGlyGluLysGlyProCysCysAlaCysProLysThrGluAlaLysGln
AACCCCAAGACTGAGGTGCCAAAGACTTGTGGTGGGGAAAAGGGCCCTTGCTGCGCCTGCCCCAAAACTGAAGCCGAAGCAG    2250
                    ⊢━━━━━━⊣
                      ⓢ
                                               700
AlaGluLysGlyAlaGluAlaGluTyrArgLysValPheGluAsnPheHisAsnSerIlePheValProArgPro
GCCGAGAAGGGAGCAGAGGCTGAATACCGCAAAGTCTTTGAGAATTTCCACAACAGCATCTTCGTGCCCAGACCT    2250

730
GluArgLysArgArgAspArgAspValMetGlnAlaAlaAsnThrThrSerSerArgSerArgAsnThrThrAlaAla
GAAAGGAAGCGGAGACGGGAGATGTCATGCAAGCTGCCAACACCACCTCCAGCCGAAGCAGAAACACCACGGCCGCA    2400
⊢━━━━━━━━━━━━━━━━━⊣
  β subunit
           ━━━━━━━━━━━━━━━━━━━━━━━━━━━
                    720
                         ⑥
                                   750
AspThrTyrAsnIleThrAspProGluGluLeuGluThrGluTyrProPheThrSerArgValSerArgValAspAsnLys
GACACCTACAACATCACCGACCCGGAAGAGCTGGAGACAGAGTACCCCTTTCTTGAGAGCAGAGTGGATAACAAG   2400

770                                    780
GluArgThrValIleSerAsnLeuArgProPheThrLeuTyrArgIleAspIleHisSerCysAsnHisGluAla
GAGAGAACTGTCATTTCTAACCTTCGGCCCTTTCACATTGTACCGCATAGATATCCACAGCTGCAACCACGAGGCT    2550

800
GluLysLeuGlyCysSerAlaSerAsnPheValPheAlaArgThrMetProAlaGluGlyAlaAspAspIlePro
GAGAAGCTGGGCTGCAGCGCCTCCAACTTCGTCTTTGCAAGGACTATGCCCGCAGAAGGAGCAGATGACATTCCT    2550

810                                   820                            830
GlyProValThrTrpProGluProArgProGluLeuLeuLysTrpProGluProProGluProAsnProAsnGly
GGGCCCGTGACCTGGCCCGAGCCCAGGCCTGAGCTGCTGAAATGGCCGGAACCTGAGAATCCCAATGGA       2700

850
LeuIleLeuMetTyrGluIleLysTyrGlySerGlnValGluAspGlnArgGluCysValSerArgGlnGluTyr
TTGATTCTAATGTATGAAATAAAATACGGATCACAAGTTGAGGATCAGCGGGAGTGTGTCAGACAGGAATAC    2700
```

FIG. 4D

```
                                                                    880
ArgLysTyrGlyGlyValAlaLysLeuAsnArgLeuAsnProGlyAsnTyrThrAlaArgIleGlnAlaThrSerLeu
AGGAAGTATGGTGGAGGGCCAAGCTAAACCGGCTAAACACCGGGAACTACACAGCCCGGATTCAGGCCACATCTCTC 860                     870

2850
SerGlyAsnGlySerTrpThrAspArgValPhePheTyrValGlnAlaLysThrGlyTyrGluAsnPheIleHis
TCTGGGAATGGGTCGTGGACAGATCCTGTCTTCTTCTATGTCCAGGCCAAAACAGGATATGAAAACTTCATCCAT 890                      900
                                                                              930
LeuIleIleAlaAlaLeuProValAlaValLeuLeuIleLeuValGlyGlyLeuValIleMetLeuTyrValPheHisArg
CTGATCATCGCTGCCCTGCCCGTCGTGTTGCTCATCCTCGTGGGAGGGTTGGTGATTATGCTGTACGTCTTCCATAGA 910                      920                                 3000
LysArgAsnAsnSerArgLeuGlyAsnGlyValLeuTyrAlaSerValAsnProGluTyrPheSerAlaAlaAsp
AAGAGAAATAACAGCAGGCTGGGGAATGGCGTGCTCTGTGTATGCCTCTGTGAACCCGGAGTACTTCAGCGCTGCTGAT 940                     950                                       980
ValTyrValProAspGluTrpGluValAlaArgGluLysIleThrMetSerArgGluLeuGlyGlnGlySerPhe
GTGTACGTTCCTGATGAGTGGGAGGTGGCTCGGGAGAAGATCACCATGAGCCGGGAACTTGGGCAGGGGTCGTTT 960                      970                                 ↓
                                                                              3150
GlyMetValTyrGluGlyValAlaLysGlyValValLysAspGluProGluThrArgValAlaIleLysThrVal
GGGATGGTCTATGAAGGAGTTGCCAAGGGTGTGGTGAAAGATGAACCTGAAACCAGAGTGGCCATTAAAACAGTG 990                          1000                                      1030
AsnGluAlaAlaSerMetArgGluArgIleGluPheLeuAsnGluAlaSerValMetLysGluPheAsnCysHis
AACGAGGCCGCAAGCATGCGTGAGAGGATTGAGTTTCTCAACGAAGCTTCTGTGATGAAGGAGTTCAATTGTCAC 1010                    1020                                      3300
HisValValArgLeuLeuGlyValCysSerGlnGlyGlnProThrLeuValIleMetGluLeuMetThrArgGly
CATGTGGTGCGATTGCTGGGTGTCTGCAGCCAGGGCCAGCCAACACTGGTCATCATGGAACTGATGACACGGGGC 1040                    1050
                                                                             1080
AspLeuLysSerTyrLeuArgSerLeuArgProGluMetGluAsnAsnProValAlaProProLeuSer
GATCTCAAAAGTTATCTCCGGTCTCTGAGGCCAGAATAATCCAGTCCTAGCACCTCCAAGCCTGAGC 1060                    1070
```

FIG. 4E

```
                                    1090                                    1100
      LysMetIleGlnMetAlaGlyIleAlaAspGlyMetAlaTyrLeuAsnAlaAsnLysPheValHisArgAsp
      AAGATGATTCAGATGGCCGGAGAGATTGCAGACGGCATGGCATACCTCAACGCCAATAAGTTCGTCCACAGAGAC    3450
                1110                                    1120                                    1130
      LeuAlaAlaArgAsnCysMetValAlaAlaGluAspPheThrValLysIleGlyAspPheGlyMetThrArgAspIle
      CTTGCTGCCCGGAATTGCATGGTAGCGGCAGAGGATTTCACAGTCAAAATCGGAGATTTTGGTATGACGCGAGATATC
                                    1140                                    1150
      TyrGluThrAspTyrTyrArgLysGlyGlyLysAlaMetLeuProValArgTrpMetSerProGluSerLeuLys
      TATGAGACAGACTATTACCGGAAAGGAGGGAAAGCCATGCTGCCCGTGCGCTGGATGTCTCCTGAGTCCCTCAAG    3600
                1160                                    1170                                    1180
      AspGlyValPheThrThrThrTyrSerAspValTrpSerPheGlyValValLeuTrpGluIleAlaThrLeuAlaGlu
      GATGGAGTCTTCACCACTACTTACTCGGACGTCTGGTCCTTCGGGGTCGTCTTGTGGGAGATCGCCACACTGGCCGAG
                                    1190                                    1200
      GlnProTyrGlnGlyLeuSerAsnGluGlnValLeuArgPheValMetGluGlyGlyLeuLeuAspLysProAsp
      CAGCCCTACCAGGGCTTGTCCAACGAGCAAGTCCTTCGCTTCGTCATGGAGGGCGGCCTTCTGGACAAGCCAGAC    3750
                1210                                    1220                                    1230
      AsnCysProAspMetLeuPheGluLeuMetArgMetCysTrpGlnTyrAsnProLysMetArgProSerPheLeu
      AACTGTCCTGACATGCTGTTTGAACTGATGCGCATGTGCTGGCAGTATAACCCCAAGATGAGGCCTTCCTTCCTG
                                    1240                                    1250
      GluIleIleSerSerIleLysGluGluMetGluProGlyPheArgGluValSerPheTyrTyrSerGluGluAsn
      GAGATCATCAGCAGCATCAAAGAGGAGATGGAGCCTGGCTTCCGGGAGGTCTCCTTCTACTACAGCGAGGAGAAC    3900
                1260                                    1270                                    1280
      LysLeuProGluProGluGluLeuAspLeuGluProGluAsnMetGluSerValProLeuAspProSerAlaSer
      AAGCTGCCCGAGCCGGAGGAGCTGGACCTGGAGCCAGAGAACATGGAGAGCGTCCCCCTGGACCCCTCGGCCTCC
                                    1290                                    1300
      SerSerSerLeuProLeuProAspArgHisSerGlyHisLysAlaGluAsnGlyProGlyProGlyValLeuVal
      TCGTCCTCCCTCCCACTGCCCGACAGACACTCAGGACACAAGGCCGAGAACGGCCCCGGCCCTGGGGTGCTGGTC    4050
```

FIG. 4F

```
                1310                                    1320
LeuArgAlaSerPheAspGluArgGlnProTyrAlaHisMetAsnGlyGlyArgLysAsnGluArgAlaArgAlaLeuPro
                                        1330
CTCCGCGCCAGTCTTCGACGAGAGACAGCCTTACGCCCACATGAACGGGGGCCGCAAGAACGAGCGGGCCCTTGCCG

LeuProGlnSerSerThrCysEnd
CTGCCCCAGTCTTCGACCTGCTGATCCTTGAATCTGTGCAAACAGTAACGTGTGCGCACGCGCAGCGG        4200

GGTGGGGGGGAGAGAGTTTAACAATCCATTCACAAGCCTCCTGTACCTCAGTGGATCTTCAGTTCTGCCCT        4350

TGCTGCCCGCGGGAGACAGCTTCTCTGCAGTAAAACACATTTGGGATGTCCTTTTTCAATATGCAAGCAGCTT        4500

TTTATTCCCTGCCCAAACCCTTAACTGACATGGGCCTTTAAGAACCTTAATGACAACACTTAATAGCAACAGAGC

ACTTGAGAACCAGTCTCCTCACTCTGTCCCTGTCCCTGGGTCATTACAAAAAAACACGTTCATCCAAGGCTGTTACCT        4650

GGAAAAATAATTGCCACACCCGCCTGACACCGCCTGGGAAGCCCTTTTATCAGTTTGAGGAAGTGGCTGTCCCTGTGGCCCC

ATCCAACCACTGTACACACCCGCCTGACACCGTGGGTCATTACAAAAAAACACGTTCATCCAAGGCTGTTACCT        4650

TTATCTTTCACCTTTCTAGGGACATGAAATTTCTCCCATTTGAGAGACACGTGAATCCTCGTGTCCGGAGGCATGGG        4800

TGCCTAATTTTGCCAAAATCCTGAACTTTCTCCATTTGAGAGACACGTGAATCCTCGTGTCCGGAGGCATGGG

TGAGCATGGCAGCTGGTTGCTCCATTTGCTCTCATTGCTCTTCTGACTAGATTATTATTTGGGGGAACTGGACACAATAG        4950

GCTGCTCAAGGCCACACAGGCACACAGGTCTCATTGCTCTTCTGACTAGATTATTATTTGGGGGAACTGGACACAATAG

GTCTTTCTCTCAGTGAAGGTGGGGAGAAGCTGAACCGGC                                          4989
```

FIG. 4G

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 927 base pairs
( B ) TYPE: nucleic acid
( C ) STRANDEDNESS: single ( D ) TOPOLOGY: linear ( i i ) MOLECULE TYPE: RNA ( x i ) SEQUENCE DESCRIPTION: SEQ ID NO: 1:

| | | | | | |
|---|---|---|---|---|---|
| CUUUGUUUC | UUUUCUUCCU | CACAGACCUU | CGGGCAAGGA | CCUUCACAAG | 50 |
| GGAUGCAGUA | CAUGCUCUGG | CUGCCGUUGC | GGAUGAAGCC | CGAGGGGCAC | 100 |
| UCCUGCAUGC | ACUCGCCGUC | GUGGAUCACA | AACCCCUCGG | AGUCGCUGCU | 150 |
| CUCGGCGCUG | AGGAUGUUGG | CGCAGAAGUC | ACGGUCCACA | CAGCGCCAGC | 200 |
| CCUCAAACCU | GUAGGUGUUG | GGCGGGCAGG | CAGGCACACA | GACACCGGCA | 250 |
| UAGUAGUAGU | GGCGGCAAGC | UACACAGGCC | GUGUCGUUGU | CAGGCGCGCU | 300 |
| GCAGCUGCCC | AGGCACUCGG | GGUGGCAGCA | CUCAUUGUUC | UCGGUGCACG | 350 |
| CCCGCUUCCC | ACACGUGCUU | GGGCACAUUU | UCUGGCAGCG | GUUUGUGGUC | 400 |
| CAGCAGCGGU | AGUUGUACUC | AUUGUUGAUG | GUGGUCUUCU | CACACAUCGG | 450 |
| CUUCUCCUCC | AUGGUCCUG | GACACAGGUC | CCCACAUUCC | UUUGGGGGCU | 500 |
| UAUUCCCCAC | AAUGUAGUUA | UUGGACACCG | CAUCCAGGAU | CAGGGACCAG | 550 |
| UCCACAGUGG | AGAGGUAACA | GAGGUCAGCA | UUUUUCACAA | UCCUGAUGGC | 600 |
| CCCCGAGUA | AUGUUCCUCA | GGUUGUAAAG | CCCAAUAUCC | UUGAGAUUGG | 650 |
| UCAUCUCGAA | GAUGACCAGG | GCGUAGUUGU | AGAAGAGUUU | CCAGCCGCGG | 700 |
| AUGACCGUGA | GGUUGGGGAA | GAGGUCUCCG | AGGCUCUCGA | GGCCAGCCAC | 750 |
| UCGGAACAGC | AGCAAGUACU | CGGUAAUGAC | CGUGAGCUUG | GGGAAGCGGU | 800 |
| AGCUGCGGUA | GUCCUCGGCC | UUGGAGAUGA | GCAGGAUGUG | GAGGUAGCCC | 850 |
| UCGAUCACCG | UGCAGUUCUC | CAGGCGCUUC | AGCUGCUGAU | AGUCGUUGCG | 900 |
| GAUGUCGAUG | CCUGGCCCGC | AGAUUUC | | | 927 |

( 2 ) INFORMATION FOR SEQ ID NO: 2:

( i ) SEQUENCE CHARACTERISTICS:
            ( A ) LENGTH: 18
            ( B ) TYPE: nucleic acid
            ( C ) STRANDEDNESS: single
            ( D ) TOPOLOGY: linear ( i v ) ANTI-SENSE: yes ( x i ) SEQUENCE DESCRIPTION: SEQ ID NO: 2:

TCCTCCGGAG CCAGACTT                                       18

METHOD OF INDUCING RESISTANCE TO TUMOR GROWTH

REFERENCE TO GOVERNMENT GRANTS

This invention was funded by National Institute of Health Grants GM 33694 and CA 56309. The U.S. government may have certain rights in the invention.

BACKGROUND OF THE INVENTION

Evidence is rapidly accumulating that growth factors and their receptors play a crucial role in the establishment and maintenance of transformed phenotypes. It is well established that growth factors play a crucial role in the establishment and maintenance of the transformed phenotype. Mouse embryo cells with a targeted disruption of the type 1 insulin-like growth factor receptor (IGF-IR) genes cannot be transformed by SV40 T antigen and/or an activated Ha-ras oncogene (Sell et al., *Proc. Natl. Acad. Sci. USA* 1993, 90:11217–11221; Sell et al., *Mol. Cell. Biol.* 1994, 14:3604–3612.; Valentinis et al., *Oncogene* 1994, 9:825–831; Coppola et al., *Mol. Cell. Biol.* 1994, 14:4588–4595), that easily transform embryo cells generated from their wild-type littermates. Expression of an antisense RNA to the IGF-IR RNA in C6 rat glioblastoma cells not only abrogates tumorigenesis in syngeneic rats, but also causes complete regression of established wild type tumors (Resnicoff et al., *Cancer Res.* 1994a, 54:2218–2222, Resnicoff, M., et al., *Cancer Res.* 1994b, 54:4848–4850. Related to this findings is also the report by Harrington et al., *EMBO J.* 1994, 13:3286–3295, that IGF-I (and PDGF) protect cells from c-myc induced apoptosis; a decrease in cell death rate in tumors could certainly be an important mechanism for tumor growth (Baserga, *The Biology of Cell Reproduction*, Harvard University Press, Cambridge, Mass., 1985). Cells expressing an antisense RNA to the IGF-IR RNA or cells pre-incubated with antisense oligodeoxynucleotides to the IGF-IR RNA completely lose their tumorigenicity when injected in either syngeneic or nude mice. (Resnicoff et al., 1994a, 1994b). The injected cells were suspected of undergoing apoptosis or, at any rate, some form of cell death. Dying cells, however, are very difficult to demonstrate, because dying cells, especially in vivo, disappear very rapidly, and one is left with nothing to examine.

The importance of the IGF-I receptor in the control of cell proliferation is also supported by considerable evidence: 1) many cell types in culture are stimulated to grow by IGF-I (Goldring and Goldring, *Crit. Rev. Eukaryot. Gene Expr.* 1991, 1:301–326 and Baserga and Rubin, *Crit. Rev. Eukaryot. Gene Expr.* 1993, 3:47–61), and these cell types include human diploid fibroblasts, epithelial cells, smooth muscle cells, T lymphocytes, myeloid cells, chondrocytes, osteoblasts as well as the stem cells of the bone marrow; 2) interference with the function of the IGF-I receptor leads to inhibition of cell growth. This has been demonstrated by using antisense expression vectors or antisense oligodeoxynucleotides to the IGF-I receptor RNA: the antisense strategy was successful in inhibiting cellular proliferation in several normal cell types and in human tumor cell lines (Baserga et al., 1994, supra.); and 3) growth can also be inhibited using peptide analogues of IGF-I (Pietrzkowski et al., *Cell Growth & Diff* 1992a, 3:199–205, and Pietrzkowski et al., *Mol. Cell. Biol.* 1992b, 12:3883–3889), or a vector expressing an antisense RNA to the IGF-I RNA (Trojan et al., 1993, supra.). The IGF autocrine or paracrine loop is also involved in the growth promoting effect of other growth factors, hormones (for instance, growth hormone and estrogens), and oncogenes like SV40 T antigen and c-myb, and in tumor suppression, as in the case of WT1 (Baserga et al., 1994, supra.).

Tumors and other neoplastic tissues are known to undergo apoptosis spontaneously or in response to treatment. Examples include several types of leukemia, non-Hodgkin's lymphoma, prostate tumor, pancreatic cancer, basal and squamous cell carcinoma, mammary tumor, breast cancer, and fat pad sarcoma. Several anticancer drugs have been shown to induce apoptosis in target cells, Buttyah, R., et al., *Mol Cell Biol* 1989, 9:3473–3481; Kaufmann, S. H., *Cancer Res* 1989, 49:5870–5878; and Barry, M. A., et al., *Biochem Pharmacol*, 1990, 40:2353–2362. Certain mildly adverse conditions can result in the injured cell dying by programmed cell death, including hyperthermia, hypothermia, ischemia, and exposure to irradiation, toxins, and chemicals. It should be noted that many of these treatments will also result in necrosis at higher doses, suggesting that mild injury to a cell might induce cell suicide, perhaps to prevent the inheritance of a mutation, while exposure to severe conditions leads directly to cell death by necrosis.

However, the death process is difficult to observe due to the rapidity of the process and the reduced amount of inflammation. For these reasons, quantification of apoptosis is often difficult. A method of measuring the duration of the histologically visible stages of apoptosis (3 hours in normal rat liver) and a formula by which to calculate the cell loss rate by apoptosis, is set forth by Bursch, W., et al., *Carcinogenesis* 1990, 11:847–853.

Nonetheless, testing agents such as growth factors and growth factor receptors for their ability to maintain or suppress transformed phenotypes remains difficult. In order to obtain an accurate account of the tumor suppressive ability, testing should be performed in vivo. Therapies such as direct injection or implantation of toxic treatments, tissue samples, and chemotherapy often jeopardizes the overall health of the patient. The present invention provides a method of inducing resistance to tumor growth with markedly reduced side effects to the patient.

SUMMARY OF THE INVENTION

The present invention is directed to a method of inducing resistance to tumor growth comprising placing tumor cells into a culture supplemented with an agent in a diffusion chamber thereby producing a cell-containing chamber, inserting the cell-containing chamber into a mammal for a therapeutically effective time, thereby inducing resistance to tumor growth.

BRIEF DESCRIPTION OF THE FIGURES

FIGS. 4A through 4G provide the amino acid and nucleotide sequence of IGF-1 receptor.

DETAILED DESCRIPTION OF THE INVENTION

The present invention is directed to a method of inducing resistance to tumor growth comprising placing tumor cells into a culture supplemented with an agent in a diffusion chamber thereby producing a cell-containing chamber, inserting the cell-containing chamber into a mammal for a therapeutically effective time, thereby inducing resistance to tumor growth. Mammals subsequently subcutaneously challenged with wild-type tumor cells are resistant to the tumor cells. In addition, regression of already established tumors is evidenced. The present invention is also directed to a method of inducing apoptosis.

Apoptosis, for purposes of the present invention, is defined as cell death, including and not limited to regression of primary and metastatic tumors. Apoptosis is a programmed cell death which is a widespread phenomenon that plays a crucial role in the myriad of physiological and pathological processes. There exists a homeostatic control of cell number thought to result from the dynamic balance between cell proliferation and cell death. Necrosis is an accidental cell death which is the cell's response to a variety of harmful conditions and toxic substances. Apoptosis, morphologically distinct from necrosis, is a spontaneous form of cell death that occurs in many different tissues under various conditions. This type of cell death typically occurs in scattered cells and progresses so rapidly it is difficult to observe.

The cell death process of apoptosis occurs in two stages. The cell undergoes nuclear and cytoplasmic condensation, eventually breaking into a number of membrane-bound fragments containing structurally intact apoptotic bodies, which are phagocytosed by neighboring cells and rapidly degraded. Apoptosis is observed in many different tissues, healthy and neoplastic, adult and embryonic. Death occurs spontaneously, or is induced by physiological or noxious agents. Apoptosis is a basic physiological process that plays a major role in the regulation of cell populations.

Cells used in the methods of the present invention include and are not limited to autografts, allografts, syngeneic, non-syngeneic and xenografts. Cells which may be cultured in a medium supplemented with an agent in a diffusion chamber include any type of cell which upon apoptosis induces resistance to tumor growth, including and not limited to tumor cells. Preferably, tumor cells are placed in a diffusion chamber which is implanted in a mammal, wherein the tumor cells may preferably be the same type of tumor to which resistance is induced. However, an embodiment of the present invention includes tumors cultured in a diffusion chamber which are of a different type than the tumor to which resistance is granted. In addition, any type of cell which undergoes apoptosis and induces resistance to tumor growth is useful in the present invention.

The agent which supplements the culture medium in the diffusion chamber may be selected from any apoptosis-inducing agent, such as and not limited to, an antisense sequence coding for a cell growth factor or cell growth factor receptor, culturing said cells for a therapeutically effective time thereby producing therapeutically induced cells, locating the therapeutically induced cells. An apoptosis-inducing agent, for purposes of the present invention, is an agent which causes cell death of the cells in the chamber such that the cell death has a growth inhibiting effect, i.e. a resistant effect, on a tumor or tumors in the mammal in which the chamber is placed. Tumors which are treatable with the methods of the present invention may be primary or secondary, benign, malignant, metastatic, or micrometastatic tumors.

Therapeutically effective doses of the apoptotic-inducing agents will be about that of the drugs alone; dosages will be set with regard to weight, and clinical condition of the patient. The proportional ratio of active ingredient to culture medium will naturally depend on the chemical nature, solubility, and stability of the compounds, as well as the dosage contemplated. The culture medium is also pharmaceutically acceptable.

Tumorous tissue may be placed in culture together with an agent such as an antisense sequence or sequences of a cell growth factor or cell growth factor receptor. Antisense sequences for cell growth factors and cell growth factor receptors include and are not limited to antisense sequences complementary to sequences for insulin growth factor-1 (IGF-1), insulin growth factor-II (IGF-II), insulin growth factor-1 receptor (IGF-IR), platelet derived growth factor (PDGF), epidermal growth factor (EGF), fibroblast growth factor (FGF), toxins such as diphtheria toxin and gliotoxin, anticancer drugs such as etoposide, cisplatin, camptothecin, and the like, and chemicals such as 1,2-dimethylhydrazine, methylazoxymethanolacetate, 1-methyl-4-phenylpyridinium, dimethylnitrosamine, and acetaminophen, and the like. Antisense sequences for one or more of the factors and/or receptors may be used in the methods of the present invention. Accordingly, antisense sequences for the factors and/or receptors may be used in a mixture or in combination. In addition to antisense sequences, additional agents which may be useful in supplementing the culture medium of the diffusion chamber include and are not limited to etoposide, and tumor necrosis factor, and exposing tumor cells to conditions such as radiation including ionizing radiation, temperature changes such as hypothermia and hyperthermia, and ischemia, and the like, prior to placing the diffusion chamber containing cells in the patient. In cases where the tumor cells are exposed to such conditions, the condition is defined for purposes of the present invention as an agent, an apoptosis-inducing agent.

In the case of antisense sequences useful in the present invention against insulin growth factor 1 receptor, IGF-1R, antisense sequences may be selected from the following non-limiting oligonucleotides: an RNA oligo to codons 1–309, SEQ ID NO: 1. The antisense oligoribonucleotide, which may be produced from an expression vector, comprises a sequence complementary to condons 1 to 309, or oligos within the 1 to 309 condons, of the IGF-1 receptor, SEQ ID NO: 1 and FIGS. 4A–4G. In addition, mismatches within the 1 to 309 RNA sequence are within the scope of the invention. A DNA antisense oligo to nucleotides −29 to −24, of the IGF-1R signal sequence, for example SEQ ID NO: 2 is also within the scope of the present invention. The signal sequence of IGF-1 receptor is a 30 amino acid sequence. Contemplated by this definition are fragments of oligos within the 30 amino acid signal sequence. Alternatively, fragments of oligos within SEQ ID NO: 2 are also contemplated.

Tumorous tissue may be excised from the patient in which the diffusion chamber will be inserted, however, tumorous tissue from another source, and/or that which has been cultured in vitro, may also be used together with an antisense sequence for a cell growth factor or cell growth factor receptor or other agent. The tumor cells are cultured for a therapeutically effective amount of time such that apoptosis of these cells is induced thereby causing resistance to tumor growth.

Before placing the cell-containing diffusion chamber into a mammal, cells may be gently dissociated with trypsin, incubated with an agent, and placed in the chamber. The chamber may then be implanted. Accordingly, toxic treatments to the cells are performed in vitro thereby eliminating toxicity to the host mammal. In addition, cells may be placed into culture in a chamber and the chamber directly implanted into a mammal.

The present invention employs the use of a diffusion chamber, in which the cells are contained. Cells are impermeable to a filter fitted on the diffusion chamber; they cannot leave or enter the chamber. The filter on the diffusion chamber has pores in the size range of about 0.25 µm or smaller, preferably about 0.1 µm in diameter. (Lange et al., *J. Immunol.* 1994, 153:205–211 and Lanza et al., *Transplantation*, 1994, 57:1371–1375), incorporated herein by reference in their entirety. Accordingly, cell death or apoptosis, can be quantitatively determined. The use of a diffusion chamber can be extended to other cell lines, even non-syngeneic, and even from different species, because of the rapidity with which cell death occurs, about 24 hours, well before any immune reaction could be established. Indeed, 3 types of cells with an intact number of IGF-IRs (human melanoma, rat rhabdomyosarcoma and murine p6 cells), double in number in 24 hours, regardless of whether they are syngeneic or not, while cells with decreased number of IGF-IRs, die. The diffusion chambers may be useful to study other types of cell death, induced by a variety of agents, as shown in the present invention by the massive apoptosis induced by etoposide on wild type C6 cells in vivo.

Diffusion chambers useful in the present invention include any chamber which does not allow passage of cells between the chamber and the mammal in which it is implanted, however, permits interchange and passage of factors between the chamber and the mammal. The chamber may allow for multiple and sequential sampling of the contents, without contamination and without sacrificing the mammal, therefore significantly reducing the number of implantation procedures performed on the mammal.

Figure 3:
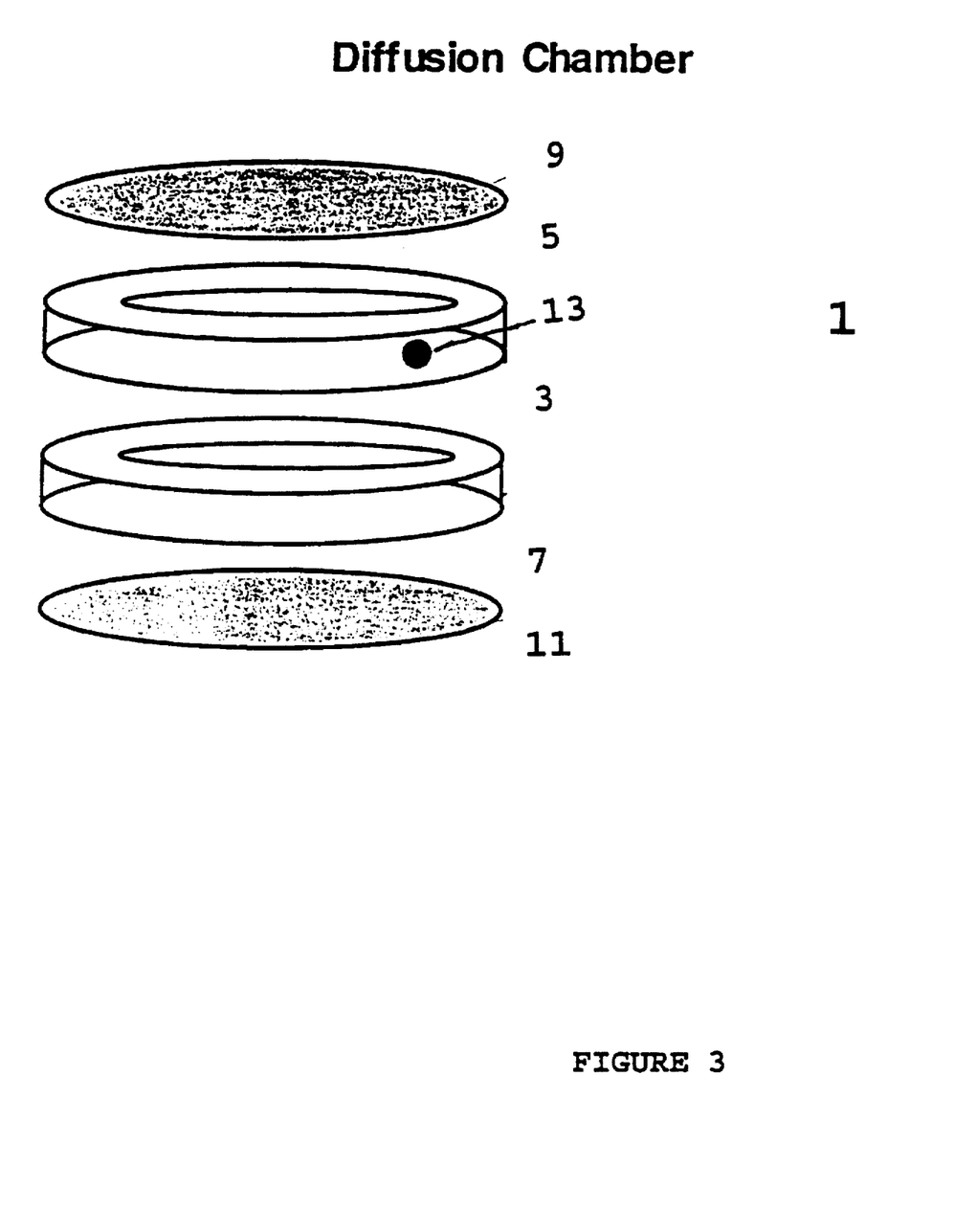
FIG. 3 is a schematic illustration of a diffusion chamber.
Figure 4A:
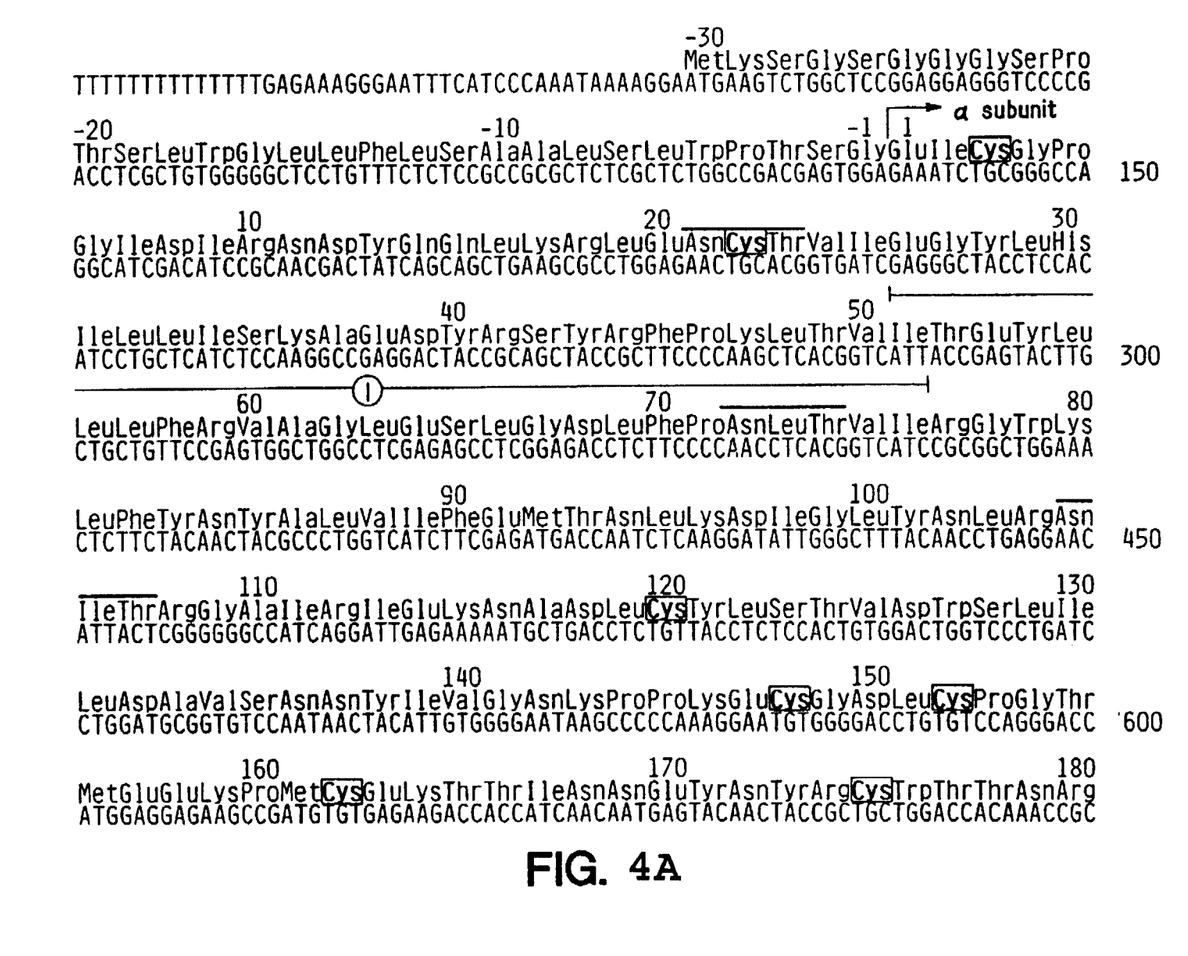
Figure 4C:
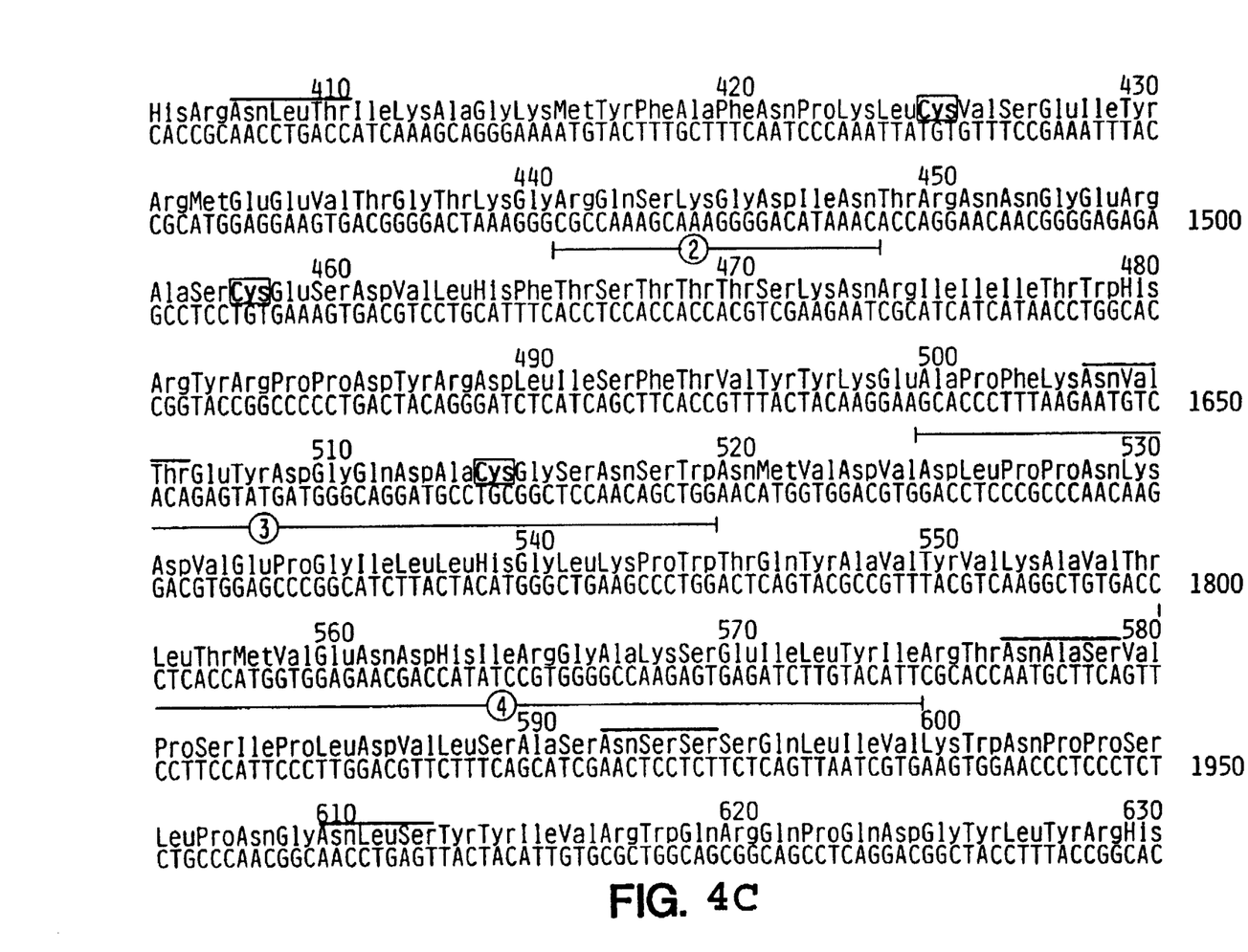
Figure 4D:
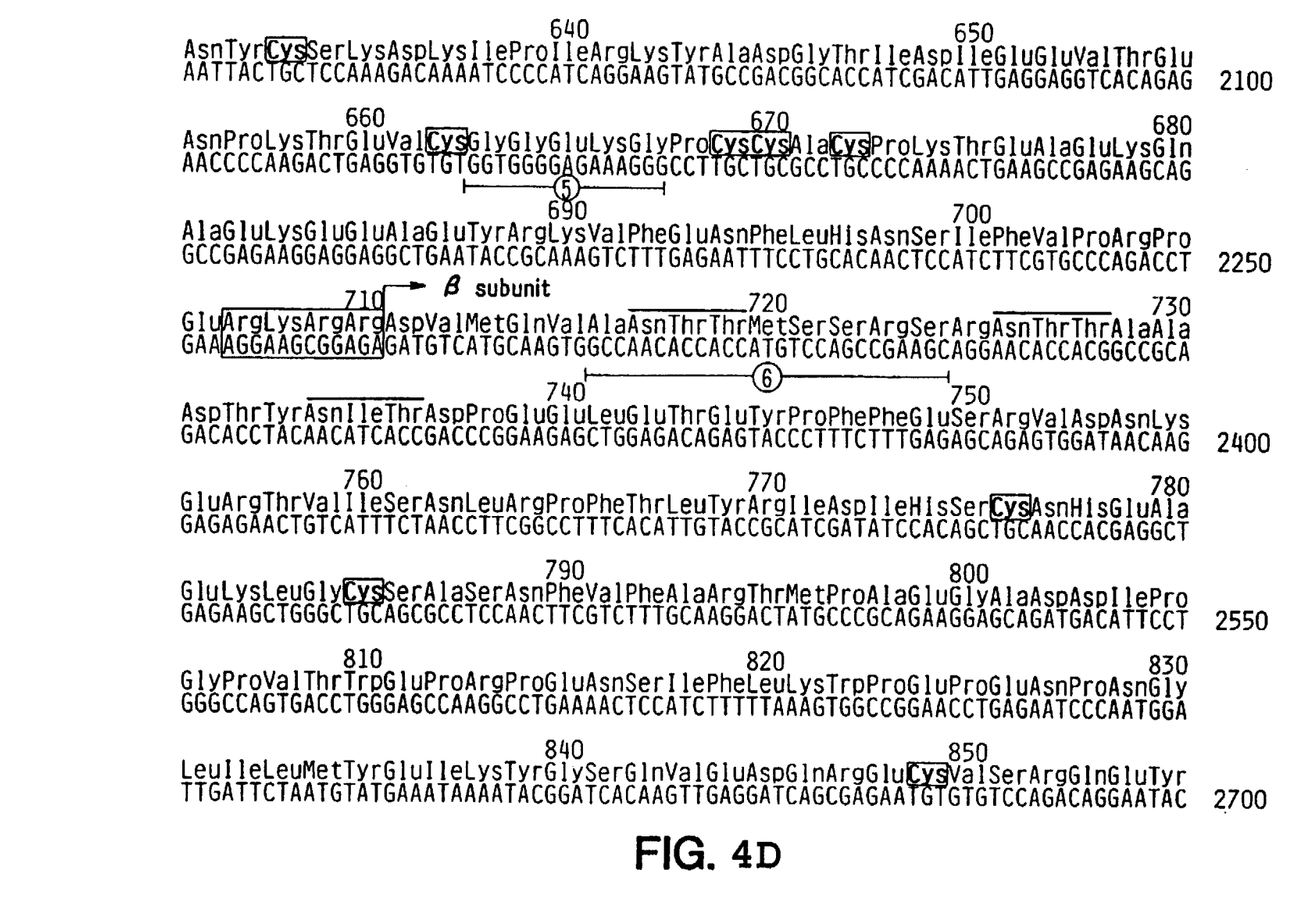
Figure 4E:
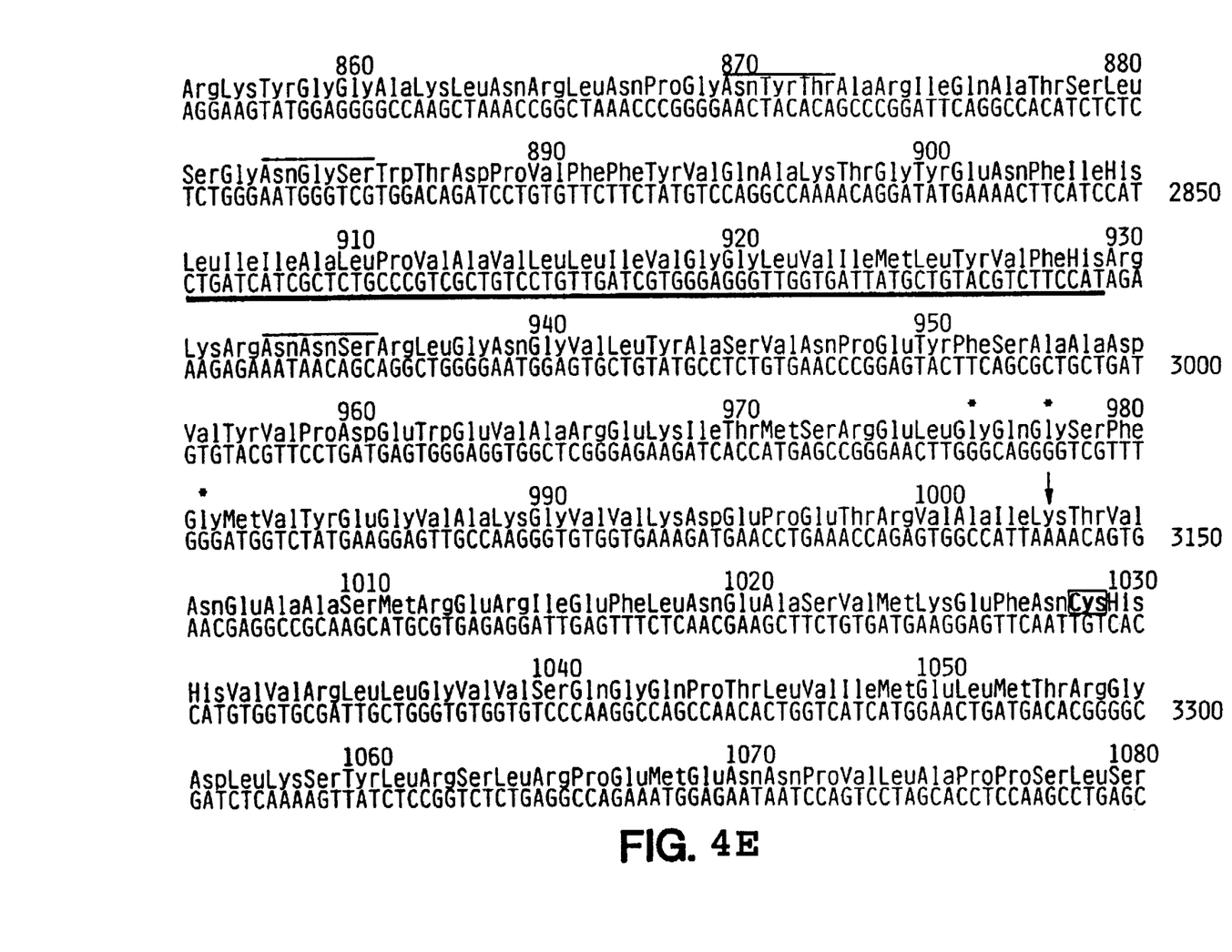
Figure 4F:
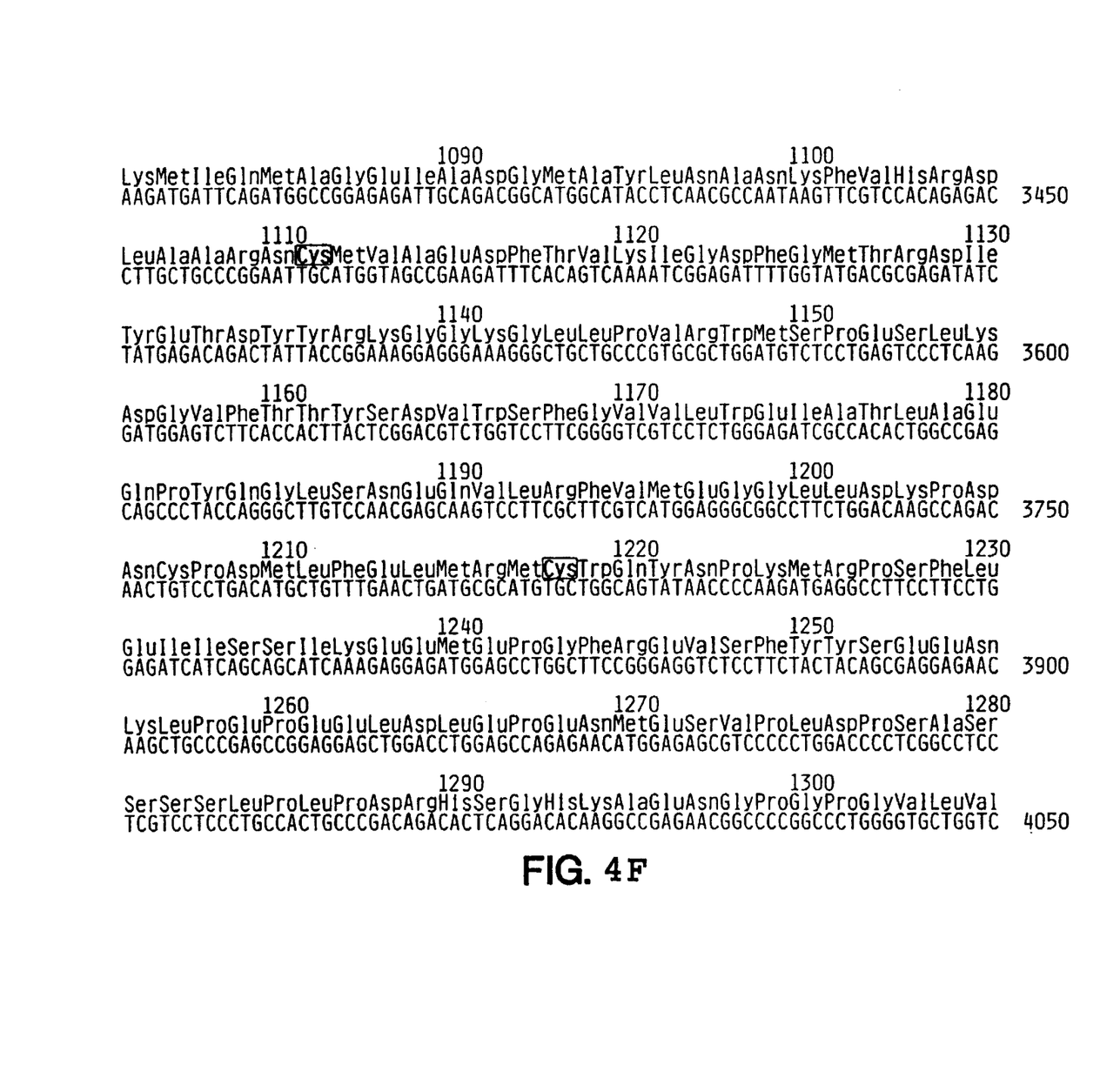
Figure 4G:
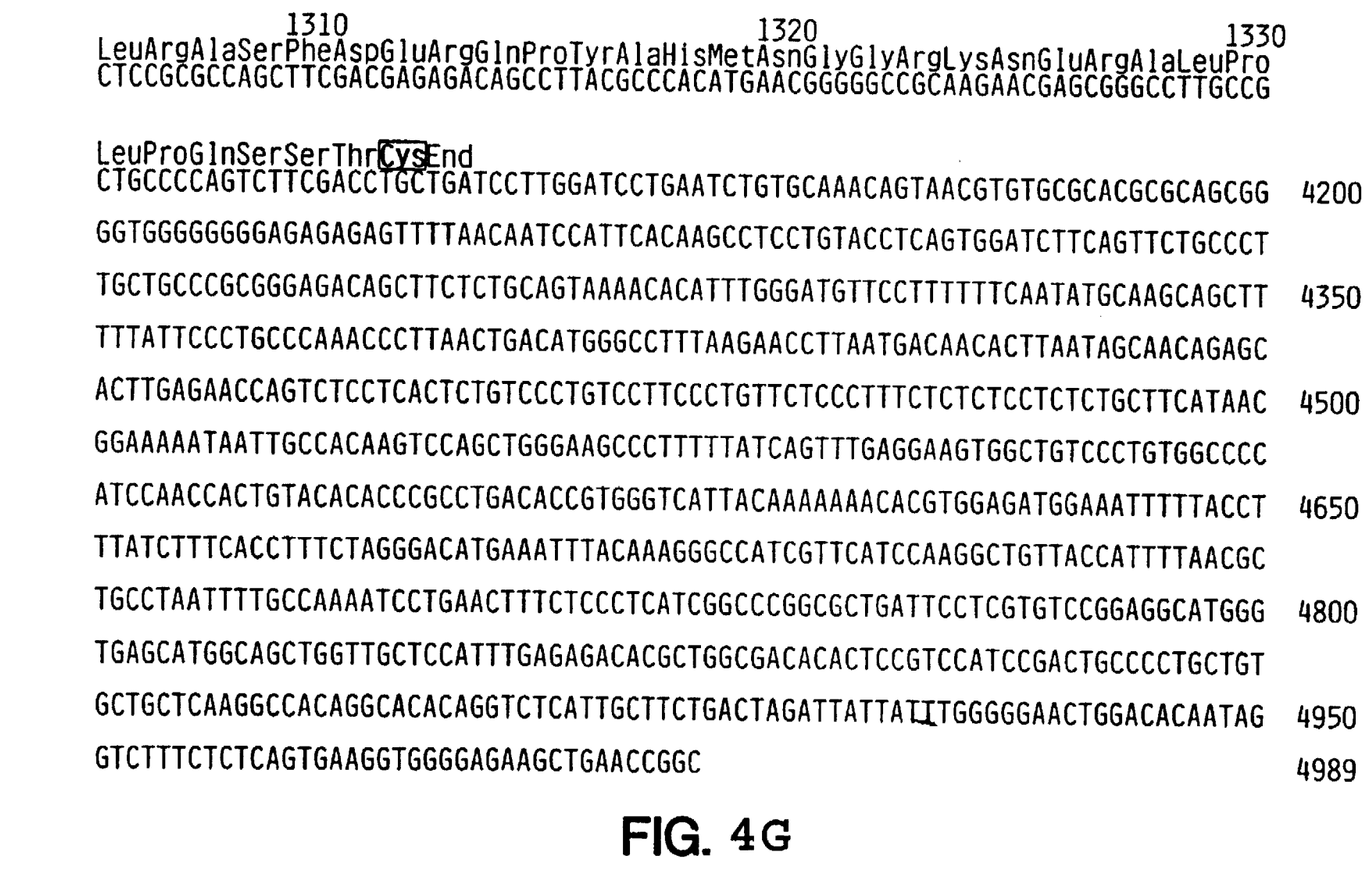

Referring to FIG. 3, the diffusion chamber (1) may have a chamber barrel (3) having two ends, a first end (5) and a second end (7). The barrel may be comprised of one or more rings secured together by non-toxic means. The chamber is fitted at each end with a filter, a first filter (9) and a second filter (11). The filters are porous to factors such that the factors may pass between the chamber and the mammal. The filter pores size may be about 0.25 µm or smaller, preferably about 0.1 µm. The filters may be made of plastic, teflon, polyester, or any inert material which is strong, flexible and able to withstand chemical treatments. The filters may be secured in position with rubber gaskets which may also provide a tighter seal. On the barrel portion of the chamber, an opening (13) is provided which may be covered by a cap which is accessed from outside of the mammal's body once the chamber is implanted. The cap may be screw on type of self sealing rubber and fitted to the opening. Sampling of the chamber contents may thus be performed by accessing the opening by removing the cap on the outside of the mammal's body and inserting an ordinary needle and syringe. The chamber may be made of any substance, such as and not limited to plastic, teflon, lucite, titanium, or any inert material, which is non-toxic to, and well tolerated by, mammals. In addition, the chambers should be able to survive sterilization.

The chamber may be implanted in the following non-limiting ways: subcutaneously or intraperitoneally, for example. The chamber may be removed about 24 to about 30 hours after implantation. Alternatively, a refillable chamber may be employed such that the chamber may be re-used for treatments and emptied following treatments.

Tumors treatable with the methods of the present invention include and are not limited to melanoma, prostate, ovary, mammary, lungs, and smooth muscle tumors; as well as cells from glioblastoma, bone marrow stem cells, hematopoietic cells, osteoblasts, epithelial cells, fibroblasts.

The present invention authenticates the importance of agents, such as IGF-IR, in the growth of tumor cells, and establishes: 1) a decrease in the number of IGF-IRs, brought about by antisense strategies, causes massive cell death in vivo. This is true of several cell lines, including a human melanoma cell line; 2) the mechanism of cell death is apoptosis; 3) a decrease in the number of receptors has an inhibitory effect on growth in vitro, but is much more effective in vivo, because of the massive cell death. IGF-IR protects tumor cells against cell death in vivo.

For purposes of the present invention, mammals include and are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

The following examples are illustrative but are not meant to be limiting of the invention.

EXAMPLES

Example 1

Tumor Cell Lines

The C6 rat glioblastoma cell line was used in this experiment. The C6 cell line is syngeneic in BD-IX rats (Charles River Breeders Laboratories, Boston, Mass.). This cell line has been described in detail by Trojan et al., *Science* 1993, 259:94–97; Resnicoff et al., *Cancer Res.* 1994a, 54:2218–2222; Resnicoff, M., Coppola, D., Sell, C., Rubin, R., Ferrone, S. and Baserga, R., *Cancer Res* 1994b, 54:4848–4850; Trojan et al., 1992, supra, the disclosures of which are hereby incorporated by reference in their entirety. Two cell lines derived from C6 cells were also used, one expressing an antisense RNA to the IGF-IR RNA, and a control one expressing a sense RNA. Both cell lines were characterized by Resnicoff et al. (1994a, 1994b), incorporated herein by reference in its entirety. Other cell lines used were a human melanoma cell line, FO-1, and a rat rhabdomyosarcoma cell line, BA 1112 (Martin et al., *Eur. J. Cancer Clin. Oncol.* 1983, 19:791–797, incorporated herein by reference in its entirety). For FO-1 and BA 1112 cell lines, wild type cells were used, cells expressing sense and cells expressing antisense RNA to the IGF-IR RNA. The plasmids used and their effect on the number of IGF-I receptors have been described by Resnicoff et al., *Cancer Res.* 1994a, 5:2218–2222, incorporated herein by reference in its entirety. The cells were pre-incubated at 39° C. for 24 hours, before inoculation in the diffusion chambers.

Cells were passaged in RPMI 1640 supplemented with 5% calf serum and 5% fetal bovine serum. $8 \times 10^4$ cells were plated in 35 mm dishes in 10% serum; after 12 hours, the growth medium was removed and replaced with serum-free medium supplemented with 0.1% bovine serum albumin (fraction V) and 1.0 µM ferrous sulfate, with or without IGF-1 (10 ng/ml), as disclosed by Resnicoff et al., *Cancer Res.* 1994a, 5:2218–2222, incorporated herein by reference in its entirety.

Balb/c 3T3 are 3T3 cells, passaged for several years, and p6 cells are Balb/c 3T3 cells stably transfected with, and overexpressing a human IGF-IR cDNA (Pietrzkowski et al., *Cell Growth & Diff.*, 1992a, 3:199–205, incorporated herein by reference in its entirety. (tsA)R− and (tsA) R+ cells have been described by Sell et al., *Proc. Natl. Acad. Sci. USA* 1993, 90:11217–11221, (tsa)R− has no IGF-I receptors, while (tsa)R+ 1 overexpresses a human IGF-IR cDNA. Both (tsa) R− and (tsa) R+ express SV40 T antigen.

The number of IGF-I receptors in cells expressing an antisense RNA to the IGF-IR RNA, or in wild type cells treated with antisense oligodeoxynucleotides, is decreased by about 60–70% (Pietrzkowski et al., *Cell Growth & Diff.* 1992, 3:199–205 and Resnicoff et al., 1994a, 1994b) incorporated herein by reference in their entirety.

Oligodeoxynucleotides

The antisense oligodeoxynucleotide used is set forth in SEQ ID NO: 2, a DNA oligo to nucleotides −29 to −24 of the IGF-1R signal sequence. The control oligodeoxynucleotide was a mixture of random mismatchings at each nucleic acid position of the −29 to −24 signal sequence. Both oligos were of the phosphorothioate type and were provided by Lynx Therapeutics (Hayward, Calif.). The wild type C6 rat glioblastoma cells were incubated with antisense oligodeoxynucleotides to the IGF-IR RNA are shown in Table 1. The antisense oligo exerts a 50% inhibition in the growth of C6 cells, while the control oligo is totally inactive.

TABLE 1

Effect of an Antisense Oligodeoxynucleotide on the Growth of C6 Glioblastoma Cells in vitro

| conditions | number of cells × $10^4$ |
| --- | --- |
| serum-free medium | 21.0 ± 0.6 |
| serum-free medium + sense | 21.8 ± 0.5 |
| serum-free medium + antisense | 15.4 ± 0.9 |
| serum-free medium + IGF-I | 29.9 ± 0.7 |
| same + sense oligo | 28.4 ± 0.3 |
| same + antisense oligo | 13.4 ± 0.6 |

The number of cells was determined 48 hours after plating, and each number is the average (with standard deviation) of triplicates. The concentration of IGF-I was 10 ng/ml. The concentration of oligodeoxynucleotides was 120 µg/ml.

Diffusion Chamber

Diffusion chambers were constructed from 14 mm Lucite rings with 0.1 µm pore-sized hydrophilic Durapore membranes (Millipore, Bedford, Mass.). The diffusion chambers were sterilized with ethylene oxide prior to use. After the cells were pre-incubated for 24 hours according to the methods of Resnicoff et al., 1994a, incorporated herein by reference in its entirety, and as set forth above, they were placed into the chambers, which were then inserted into the subcutaneous tissue of rats, under anesthesia with Halothane (inhalant). This procedure was repeated for C6 derivative cells expressing antisense RNA to IGF-IR RNA, C6 derivative cells expressing sense RNA to IGF-IR RNA, FO-1, and BA 11112 cell lines.

Figure 1:
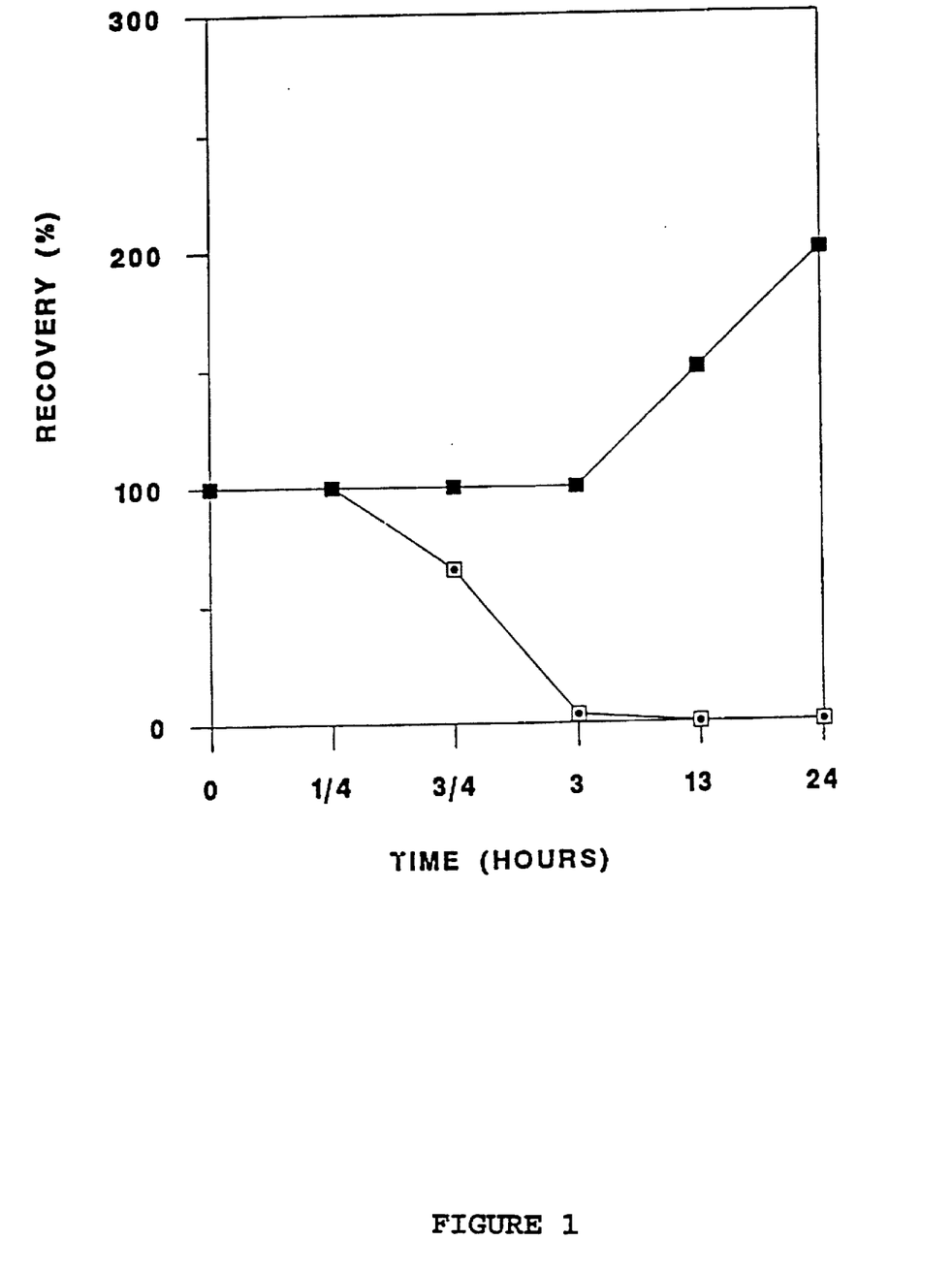
FIG. 1 is a graph of the survival of C6 rat glioblastoma cells in diffusion chambers. Three cell lines were used: wild type C6 cells, and C6 cells stably transfected with either a sense or an antisense RNA to the IGF-I receptor RNA (Resnicoff et al. 1994a and 1994b). $5 \times 10^5$ cells were inoculated in each chamber and the number of cells recovered was determined at the intervals indicated on the abscissa. Close squares: wild type or sense cells (the curves were superimposable); open squares: antisense cells. The recovery is expressed as percentage of cells inoculated.

Aliquots of $5 \times 10^5$ cells were placed in diffusion chambers, that were then inserted in the subcutaneous tissue of syngeneic rats, and removed at various intervals thereafter. The number of cells in each chamber were counted, also the percentage of cells stained by trypan blue, and finally, the residual cells were plated in tissue culture dishes. Cells stably expressing the antisense RNA rapidly died in the diffusion chambers, most of the cells being dead after only 3 hours (FIG. 1), while wild type and sense cells doubled in number in 24 hours, at which time only an occasional antisense cell could still be recovered from the chambers.

Figure 2:
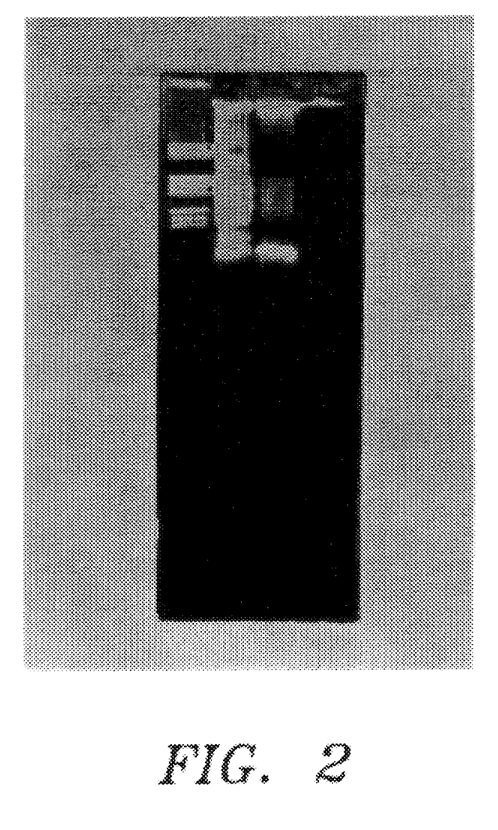
FIG. 2 is a DNA ladder of apoptotic cells. Antisense C6 cells were placed in diffusion chambers for 40 minutes, the DNA was extracted and displayed as described in Example 1.

In one experiment, antisense C6 cells were suspended in 10% serum before placing them into a diffusion chamber; all the cells were dead by 24 hours. The antisense cells were examined for evidence of apoptosis by DNA extraction and visualization on ethidium bromide-stained gels. FIG. 2 shows the typical DNA ladder of apoptotic cells, from a sample taken 40 minutes after introduction of the antisense cells into the diffusion chambers.

When the wild type C6 cells, previously incubated with the antisense oligo, were placed in a diffusion chamber and inserted into the subcutaneous tissue of rats, the results were much more impressive, as most of the cells were dead by 24 hours (Table 2), whereas cells incubated with the control oligo doubled in number. These last two experiments indicate that the IGF-IR is even more important in vivo than in vitro, for protection from cell death.

Because cell death occurs so rapidly and because cells in a diffusion chamber are, at least in part, protected from an immune response, Lanza et al., 1994, incorporated herein by reference in its entirety, which at any rate, would not have the time to set in, other tumor cell lines were tested in the same breed of rats. The first one tested was the FO-1 human melanoma, and its two derivative cell lines, expressing either a sense or an antisense RNA to the IGF-IR. The results are summarized in Table 2; wild type human melanoma cells and sense cells doubled in 24 hours, whereas only 1% of the antisense expressing cells could be recovered after 24 hours. Other cell lines were tested, and the results are summarized also in Table 2. Note that the cell recovery is the real measure of growth and survival, since viability of the recovered cells (as determined by trypan blue) was close to 100%. These experiments show that: 1) cell death in diffusion chambers can also be achieved by pre-incubating the cells with antisense oligodeoxynucleotides to the IGF-IR RNA; and 2) that cell death in diffusion chambers can also be studied with non-syngeneic cell lines, in fact even with cells of other species. Thus, both wild type human melanoma cells, wild type rat rhabdomyosarcoma cells and murine p6 cells double in number after 24 hours in the diffusion chambers, while antisense melanoma and rhabdomyosarcoma cells and 3T3-like cells without IGF-IRs, die.

TABLE 2

Growth of Several Cell Lines in Diffusion Chambers

| cell line | percentage recovery |
| --- | --- |
| C6 rat glioblastoma | 195 |
| + random oligo | 189 |
| + antisense oligo | 0 |
| + etoposide | 0.025 |
| FO-1 human melanoma | |
| wild type | 200 |
| sense plasmid | 200 |
| antisense plasmid | 1.4 |

TABLE 2-continued

Growth of Several Cell Lines in Diffusion Chambers

| cell line | percentage recovery |
|---|---|
| BA 1112 rat rhabdomyosarcoma | |
| wild type | 200 |
| sense plasmid | 200 |
| antisense plasmid | 0 |
| mouse melanoma B16 | |
| wild type | 214 |
| sense plasmid | 198 |
| antisense plasmid | 0.10 |
| p6 cells (3T3 overexpressing the IGF-IR) | 186 |
| T/R- (receptorless 3T3) | 0 |

The C6 rat glioblastoma cells were wild type cells treated or not with oligodeoxynucleotides (120 mg/ml, 24 hours before inoculation). In the case of etoposide (20 μg/ml), the C6 cells were pre-incubated with the drug for 16 hrs. prior to loading into the diffusion chamber, at which time viability was 100%. Human melanoma cells were wild type or stably transfected with either a sense or an antisense expression plasmid to the IGF-IR RNA. BA 1112 also consisted of the original wild type cell line, or cell lines stably transfected with either sense or antisense plasmids to the IGF-IR RNA. p6 cells are derived from Balb/c 3T3 cells, and express over $5 \times 10^5$ IGF-IRs per cell (Pietrzkowski et al. 1992a, 1992b), incorporated herein by reference in their entirety; T/R- cells are 3T3 cells, derived from mouse embryos with a targeted disruption of the IGF-IR genes (Sell et al., *Proc. Natl. Acad. Sci. USA* 1993, 90:11217–11221 and Sell et al., *Mol. Cell. Biol.* 1994, 14:3604–3612, incorporated herein by reference in their entirety). The percentage changes are after 24 hours in diffusion chambers in rats.

Growth Curves $5 \times 10^4$ C6 cells were plated in 35 mm dishes in 10% serum; after 4 hours the growth medium was removed and replaced with serum-free medium, supplemented with 0.1% bovine serum albumin (fraction V) and 1 μM ferrous sulfate, with or without IGF-I (10 ng/ml). Random or antisense oligodeoxynucleotides (Lynx Therapeutics, Hayward, Calif.) were added at a concentration of 120 μg/ml, directly to the medium. The cells were counted after 24 and 48 hours, using a hemocytometer. Viability was determined by trypan blue exclusion. This procedure was repeated for C6 derivative cells expressing antisense RNA to IGF-IR RNA and C6 derivative cells expressing sense RNA to IGF-IR RNA, FO-1, and BA 11112 cell lines.

Plating of cells resulted in rapid overgrowth with the wild type and sense cells, whereas antisense cells, after 24 hours in the diffusion chambers, did not produce any colony in vitro.

Determination of Apoptosis

Cells were lysed in 50 μl of lysis buffer (10 mM EDTA, 50 mM Tris pH 8, 0.5% sodium dodecyl sulfate, 0.5 mg/ml proteinase K). RNAse A (0.5 mg/ml) was added and lysates were incubated for 1 hr. at 37. Two phenol extraction (equal volumes) were performed, followed by one chloroform extraction. DNA was precipitated with two volumes of ice-cold ethanol and incubated at −80° C. for 1 hr. DNA was pelleted by centrifugation at 14,000 rpm for 10 minutes at 4° C. Pellets were air-dried for 30 minutes, resuspended in 50 μl of Tris-EDTA pH 8. DNA was electrophoresed in a 1.8% agarose gel in 1x TBE running buffer (0.05M Tris base, 0.05M boric acid, 1 mM disodium EDTA), according to the methods of Preston et al., *Cancer Res.* 1994, 54:4214–4223, incorporated herein by reference in its entirety.

Example 2

Protective and Curative Effects Against Tumor Growth By Apoptotic Cells in Diffusion Chambers C6 cells constitutively expressing an antisense RNA to the IGF-IR RNA and C6 cells pre-treated for 24 hours with antisense oligodeoxynucleotides of SEQ ID NO: 2 (−29 to −24 of the signal sequence) to the same RNA (at a concentration of 120 μg/ml) were inoculated into diffusion chambers ($5 \times 10^5$ cells per chamber in 0.2 ml of phosphate buffered saline), which were then inserted into the subcutaneous tissue of 7-week-old male BD-IX rats (Charles River Breeders Laboratories, Boston, Mass.). Untreated C6 cells, C6 cells expressing a sense RNA, and C6 cells pre-treated with a randomly mismatched oligodeoxynucleotide at each nucleic acid position of the −29 to −24 signal sequence were used as controls. Since these 3 groups of cells behaved in exactly the same manner, they are included into a single control group.

The diffusion chambers were removed at various intervals after insertion, ranging from 15 minutes to 48 hours Seven days later, the rats were challenged with $10^7$ wild type C6 cells, injected above the right hind leg. The results are summarized in Table 3. The first column (cells in diffusion chamber) indicates the treatment; the second column (% recovery) reveals the number of cells recovered expressed as percentage of cells inoculated; and the 3rd column (tumor development) gives the number of rats with tumors after challenging the animals, previously carrying the diffusion chambers, with $10^7$ wild type C6 cells, subcutaneously.

TABLE 3

| cells in diffusion chambers | % recovery | tumor development |
|---|---|---|
| control group | 200 | 15/15 (day 5) |
| antisense transfected 45 minutes | 65 | 9/9 (day 5) |
| antisense transfected 3 hours | 0–4 | 0/12 |
| antisense oligos 24 hours | 0 | 0/3 |

The first column indicates the times (in minutes and hours), after insertion, when the diffusion chambers were removed. The second column gives the percentage of live cells that were recovered. The third column reveals the appearance of wild type tumors after the rats that had received the diffusion chamber were challenged with C6 cells. Day 5 in the 3rd column is the latent period, after injection of wild type cells, for the appearance of a palpable tumor.

This example shows that resistance against subsequent challenge with homologous wild type tumor cells can be achieved either by placing in diffusion chambers cells transfected with a plasmid expressing an antisense RNA to the IGF-IR RNA (Resnicoff et al. 1994a, 1994b, supra.), incorporated by reference in its entirety, or by pre-treatment of wild type cells with antisense oligodeoxynucleotides to the IGF-IR RNA. They also indicate that resistance is conferred, when some cells are still alive (diffusion chamber left in the rat for 3 hours), i.e. it is not necessary for all cells in the chamber to die to induce resistance.

Example 3

Regression of Established Tumors by Apoptotic Cells in Diffusion Chambers

The expression plasmids used, and the C6 cells and their derivatives used in these experiments have been described in detail in the papers by Resnicoff et al., 1994a, 1994b, supra.), incorporated by reference in their entirety. The oligodeoxynucleotide sequences are provided by Resnicoff et al., the antisense was originally described in Pietrzkowski et al. 1992a, 1992b, supra., incorporated by reference in their entirety).

$10^7$ wild type C6 cells were injected subcutaneously above the right hind leg of 7-week-old male BD-IX rats. Tumors appeared at day 5, as usual. On day 7, some animals, selected at random, received diffusion chambers containing $5 \times 10^5$ C6 cells constitutively expressing an antisense RNA to the IGF-IR RNA (Resnicoff et al., 1994a, 1994b). After 24 hours, the diffusion chambers were removed, and no cells could be recovered from them. Five days later, the rats who received the diffusion chambers had tumors considerably smaller than the control animals (no chambers). Seven days after removal of the diffusion chambers (14 days after injection of wild type cells), the results were as follows:

TABLE 4

| condition | tumor development |
| --- | --- |
| control rats | 3/3 |
| treated rats | 0/3 |

Control rats were injected with $10^7$ wild type C6 cells and did not receive a diffusion chamber; treated rats received, 7 days after injection of wild type cells, a diffusion chamber with $5 \times 10^5$ C6 cells expressing an antisense RNA of SEQ ID NO: 1, to nucleic acids positions 1 to 309 to the IGF-IR RNA of FIGS. 4A–4G. In treated rats, no residual tumor could be detected at autopsy (histological examination).

This example shows that homologous tumor cells, expressing an antisense RNA to the IGF-IR RNA, inoculated into diffusion chambers, induces regression of already well established wild type tumors.

Example 4

The extent to which the tumor cells undergoing apoptosis in the diffusion chambers protect rats from the subsequent challenge with wild type C6 cells is shown in this experiment. For this purpose, different, non-syngeneic and non-homologous types of cells were inserted as usual in diffusion chambers, for a period of 24 hours. The chambers were removed, monitored for recovery of cells, and the rats were subsequently challenged with $10^7$ wild type C6 cells, following the same protocols described above. The results are summarized in Table 5, where subsequent to challenge, (−)=no tumor, (+)=no regression.

TABLE 5

| cell type in chambers | % recovery | tumor development |
| --- | --- | --- |
| Human melanoma cells (antisense) | 1.4 | (−) |
| BA-1112 (antisense) | 0 | (−) |
| (tsA)R− | 0 | (−) |
| Balb/c3T3 | 0.8 | (+) |
| (tsA)R+ | 3.2 | (+) |
| C6 cells + etoposide | 0.025 | (−) |

Human melanoma cells are FO-1 cells expressing an antisense RNA to the IGF-IR RNA (Resnicoff et al. 1994a, 1994b, incorporated by reference in their entirety); BA-1112 are cells from a transplantable rat sarcoma, also expressing an antisense RNA to the IGF-IR RNA; (tsA)R−, Balb/c 3T3 and (tsA)R+ are 3T3-like mouse cells, described in detail in Sell et al., 1994, supra., incorporated herein by reference in its entirety; C6 cells+etoposide, are wild type C6 cells pre-treated for 16 hrs with the topoisomerase inhibitor, etoposide. At the moment of loading the chamber, cells pre-treated with etoposide (20 μg/ml) were 100% viable. After 24 hrs, in vivo, only 125 cells could be recovered, of which 50% were viable, from which the percent recovery was calculated.

These experiments show that, curiously enough, when the cells placed in the diffusion chambers lacked the IGF-IR or had markedly reduced numbers, they protected rats from a subsequent challenge with wild type C6 rat glioblastoma cells, regardless of the species of cells used in the chambers. Cells with a normal number of IGF-I receptors, under the same conditions, did not display a protective effect. This seems to indicate that the protective effect of antisense strategies against the IGF-I receptor RNA cuts across species barriers.

Various modifications of the invention in addition to those shown and described herein will be apparent to those skilled in the art from the foregoing description. Such modifications are also intended to fall within the scope of the appended claims.

What is claimed is:

1. A method of inducing apoptosis of a metastatic or residual melanoma tumor comprising:
  (a) incubating in vitro a melanoma tumor cell with a modified antisense oligodeoxynucleotide sequence for insulin growth factor-1 receptor selected from the group consisting of SEQ ID NO: 1 and SEQ ID NO: 2, or a sequence that retains apoptotic activity of SEQ ID NOS: 1 or 2, wherein the cultured cell remains viable, thereby producing a melanoma tumor cell culture, wherein said tumor cell is anchorage dependent;
  (b) culturing said melanoma tumor cell culture in a diffusion chamber thereby producing a tumor cell-containing chamber, and
  (c) inserting said tumor cell-containing chamber into a mammal for a therapeutically effective time, wherein said tumor cell is not anchorage dependent, thereby inducing apoptosis of a metastatic or residual melanoma tumor in said mammal.

2. The method of claim 1 wherein a therapeutically effective time is a time permitting death of melanoma cells in said cell-containing chamber and resistance of tumor growth in the mammal.

3. The method of claim 1 wherein melanoma tumor cells of said melanoma tumor cell culture are excised from said mammal.

4. The method of claim 1 wherein melanoma tumor cells of said melanoma tumor cell culture are selected from the group consisting of autografts, allografts, and xenografts of a melanoma tumor.

5. The method of claim 1 wherein said mammal is human.

6. The method of claim 1 wherein said diffusion chamber is refillable.

7. A method of inducing apoptosis of a metastatic or residual tumor growth comprising:

(a) incubating in vitro a tumor cell with a modified antisense oligodeoxynucleotide sequence for insulin growth factor-1 receptor selected from the group consisting of SEQ ID NO: 1 and SEQ ID NO: 2, or a sequence that retains apoptotic activity of to SEQ ID NOS: 1 or 2, wherein the cultured cell remains viable, thereby producing a melanoma tumor cell culture, wherein said tumor cell is anchorage dependent;

(b) culturing said melanoma tumor cell culture in a diffusion chamber thereby producing a tumor cell-containing chamber, and (c) inserting said tumor cell-containing chamber into a mammal for a therapeutically effective time, wherein said tumor cell is not anchorage dependent, thereby inducing apoptosis of a metastatic or residual tumor in said mammal.

* * * * *